United States Patent [19]

Snow

[11] 4,413,624
[45] Nov. 8, 1983

[54] SCROTUM INSULATOR

[76] Inventor: Paul Snow, 203 Loudon Rd., Apt. 1-24, Concord, N.H. 03301

[21] Appl. No.: 271,780
[22] Filed: Jun. 8, 1981
[51] Int. Cl.³ .................. A61F 7/00; A61N 00/00
[52] U.S. Cl. ............................ 128/399; 128/386; 128/402; 128/138 R
[58] Field of Search .............. 128/138 R, 128, 386, 128/402, 399, 158–162, 132, 372, 379

[56] References Cited

U.S. PATENT DOCUMENTS

| 847,779 | 3/1907 | Jarrett | 128/158 |
|---|---|---|---|
| 2,172,866 | 9/1939 | Davis | 128/159 |
| 3,234,937 | 2/1966 | Nelkin | 128/159 |
| 3,518,995 | 7/1970 | Claff | 128/158 |
| 3,882,873 | 5/1975 | Arango | 128/402 |
| 3,909,847 | 10/1975 | Holt et al. | 128/159 |
| 3,915,150 | 10/1975 | Ray | 128/326 |

FOREIGN PATENT DOCUMENTS 452909  5/1913  France .................... 128/162

Primary Examiner—C. Fred Rosenbaum
Assistant Examiner—C. W. Shedd
Attorney, Agent, or Firm—Strimbeck Professional Association

[57] ABSTRACT

A birth control means designed to limit sperm production by effecting a slight temperature increase in the testes comprises a scrotum insulator cut from a flat sheet of a flexible insulating material to the shape of a trapezoid. Preferably the insulating material is a moisture impervious plastic film vacuum metallized to have an infrared reflective surface. The scrotum insulator is used by being held in place around the scrotum preferably as by insertion in unmodified jockey-type shorts.

6 Claims, 2 Drawing Figures

SCROTUM INSULATOR

A slight temperature increase in the scrotum maintained for several hours a day over many weeks greatly reduces sperm production. This reduction persists as long as the temperature increase is maintained. When it is stopped, sperm production not only recovers but temporarily rebounds to a higher value. Such a temperature increase can be achieved by thermally insulating the scrotum. Until now most work and suggestions in this area have been experimental and theoretical and a reasonably-priced, practical scrotum insulator of simple design and capable of wide distribution and use has not been suggested.

PRIOR ART

See: Intrascrotal Hypothermia Induced by Scrotal Insulation: Effect on Spermatogenesis, *Obstetrics and Gynecology* 29, 217, February 1967 by Derek Robinson, M.D. and John Rock, M.D. See also U.S. Pat. No. 3,518,995.

THIS INVENTION

The present invention is a scrotum insulator made of flat sheet stock and designed to conform comfortably to and effectively thermally insulate the scrotum of a user.

Objects of this invention are inter alia to provide a scrotum insulator that effectively induces a slight temperature rise in the testes when worn each day; that is comfortable and agreeable to the user; that does not unacceptably degrade in use; that is of simple but reliable construction permitting low manufacturing and distribution costs; that is unaffected by moisture in the crotch; and that is of a shape that permits manufacturing economy but nevertheless when in its three dimensional shape about the scrotum effectively covers and insulates all of the scrotum regardless of the sitting or standing position of the user.

In brief compass, the present invention is a scrotum insulator comprising a sheet of flexible insulating material in symmetric trapezoidal form, the long base of the trapezoid having a centrally located cut-out to accommodate the penis and the trapezoid being sized to fully cover the scrotum in use. Preferably the trapezoid base is six to seven inches wide, its top is one and one-half to two and one-half inches wide and its height is in the order of four and a half to five and a half inches. The cutout dimensions are preferably one and three-quarters to two and three-quarters inches at the base, three-quarters to one and one-quarter inches at the top and one-half to one inch high.

The insulator is cut from a flat or planar sheet of moisture impervious plastic film metallized to have on one side a thin infrared reflective layer which metal layer is preferably protected with a thin plastic film or top coat. A three-eighths inch or less thick layer of closed cell urethane foam can also be used.

The scrotum insulator of this invention preferably has a means for attaching the insulator to the inside of the user's undershorts. This means can be a flexible hook tape so positioned on the outside of the insulator as to minimize undesirable wrinkling and misplacement of any portion of the insulator, particularly of the "wings" of the trapezoid shape.

DRAWINGS

Figure 1:
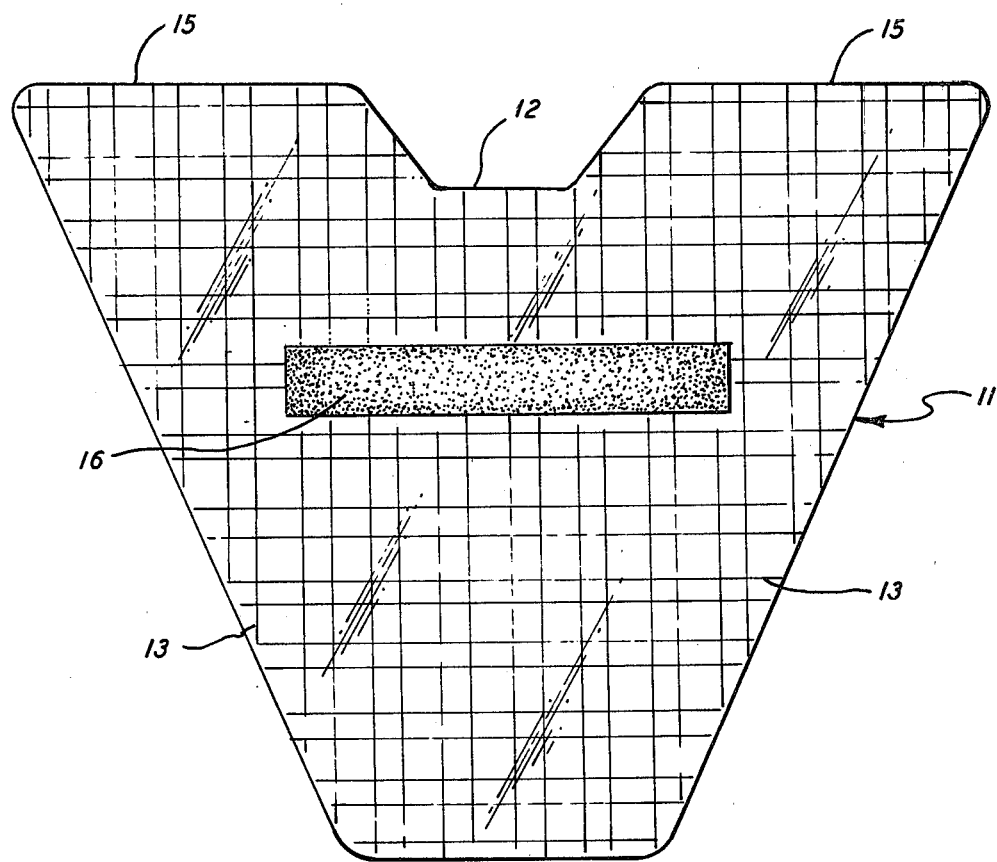
FIG. 1 illustrates the scrotum insulator of this invention.
Figure 2:
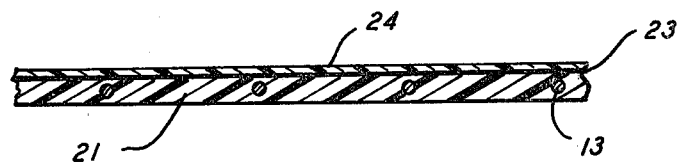
FIG. 2 is a cross sectional view of one type of insulating fabric that can be used in the practice of this invention.

Referring to the drawings, the scrotum insulator, generally indicated at 11, consists of a suitable insulating fabric cut to a trapezoid shape as shown having a cut-out 12 at the center of the base of the trapezoid designed to accommodate the penis of the wearer. For a man having a waistband of about 42 to 44 inches the trapezoid will be about six and a half inches at the base, about two inches at the top and about five inches high with the cut-out 12 being two inches at its base, one inch at its top and about three-quarters of an inch high.

As explained infra, while at first blush it may appear that the "wings" of the trapezoid are not required, it has been found that these are necessary to insure adequate insulation when the user is sitting.

A means 16 for fastening the scrotum insulator to the undershorts of the user is affixed to the outer face of the insulator. While two sided adhesive strips or other equivalent means can be used, it is preferred to use hook tape placed as shown that will engage the fabric of the undershorts and has an advantage over an adhesive surface. If the insulator when first inserted in the undershorts is not properly placed, the hook tape permits removal and replacement of the insulator whereas this may not be possible with a contact adhesive.

The hook tape preferably has a length of at least two inches, e.g. three inches, and is placed at the center of the area of the shape but at least about one inch below the cut-out 12 transverse to the center line of the trapezoid. This has been found to be about the best location for minimizing and/or overcoming the mechanical forces operating on the insulator during use that tend to cause displacement of portions of it or excessive wrinkling. If the tape is placed on the central axis of the trapezoid rather than perpendicular to it or if two pieces of tape located towards the extremity of the trapezoid are used, then the insulator is not held as well in place and/or there is discomfort to the user.

In a preferred embodiment the insulator consists of a very thin flexible sheet of polyethylene 21 reinforced with cross threads 13 in a square pattern, the inner surface of which is vacuum metallized with the thin layer of a metal such as aluminum which metal layer is preferably top-coated with a thin transparent top-coat 24 as of a polyethylene or urethane.

For regular use it is suggested that the crotch be dusted with talcum powder or other moisture absorbent, anti-abrasive material. After a correctly fitting pair of jockey undershorts are put on the insulator is inserted inside the anterior overlap of the undershorts so that there is a layer of fabric between the scrotum and the insulator. The face of the insulator which holds the fastener should point away from the body. The insulator is properly placed, when, with the wearer standing up:

(a) The base of the notch of the insulator is aligned with the junction of the penis and the scrotum;

(b) The base of the insulator extends behind both of the testicles below the scrotum;

(c) The sides of the insulator completely cover both testicles and are symmetric about the middle line;

(d) The insulator conforms to the contour of the body without folds;

(e) The top and bottom edges of the insulator are parallel to the waist.

The penis should be placed above the insulator within the cutout.

At the end of the day the insert can be removed from the undershorts and stored flat to prevent creases. As noted above the insulator should be worn continuously throughout waking hours preferably for an average of about fifteen hours or more per day.

EXAMPLES

The preferred design of the insulator was tested along with other types of insulators. The preferred insulator consists of an aluminized, reinforced polyethylene, "Sportsman Space Blanket" (King-Seeley Thermos Co., Norwich, Connecticut), cut to the size given above for a 42–44 waist. A low density close cell foam, Ensolite Type ML ( Pawtucket Foam Co., Pawtucket, Rhode Island) e.g., of approximately one-quarter inch thick was also tested. In addition eight sheets of tissue paper faced with a vinyl sheet and sixteen sheets of a rayon toweling faced with a vinyl sheet were also tested.

Thin sandwiches of porous fabric or paper and pads of open cell foams can be used in the trapezoid shape but it is necessary to appropriately waterproof them or encase them to prevent loss of their insulating value because of moisture absorption from the crotch of the wearer. Also, sandwiches of fabric or paper should be sewn or otherwise fastened together to prevent separation of the layers.

Pads thicker than one-half inch cause discomfort unless they are preformed in some manner, which is not the nature of the present invention.

All of the tests were carried out with one subject. The temperatures were measured using a thermistor applied to the skin of the scrotum at the midline with the subject sitting. Generally ninety minutes were required for the temperature to plateau. The measured temperatures ranged from 36.5 to 36.9 degrees Celsius, which agreed well with the 36.4 degrees plateau inferred from the Robinson and Rock report. It might be noted in passing that these increased temperatures do not give the user any specific sensation of warmth.

Of the materials tested, the most durable, the most comfortable and the easiest to fabricate was the reinforced aluminized polyethylene sheet.

The subject was a healthy and euspermic male with a sperm concentration of 160–200 million per cubic centimeter. Fifty-eight days after starting the experiment with the preferred embodiment and wearing it constantly almost 24 hours a day a fresh undiluted sample of the ejaculate obtained after 72 hours continence failed to contain any sperm, motile or non-motile, upon extensive microscopic examination. No pronounced or consistent effect on libido or changes in ejaculate volume were noticed during the experiment.

Wearing an insulator all day and all night is inconvenient and therefore unlikely to be tolerated by many men. Given the lowered body temperature during sleep and the tendency of undershorts to pull free of the body during sleep movements, it was not clear that use of the insulator during sleep was contributing much. Consequently fourteen months after the experiment wherein the pads were worn 24 hours a day and after recovery of normal sperm concentration confirmed by haemocytometer counting the subject undertook a replication of a waking hours only schedule. The preferred insulator of the aluminized polyethylene fabric was worn on an average of about fifteen hours a day with no day of use being less than twelve hours and with eighty-seven percent of the days being in fact fourteen hours or longer. Eighteen percent of the days were sixteen hours or more. No pronounced or consistent effect on libido or changes in ejaculate volume were noticed during the experiment. Sixty-two days after starting the experiment a fresh undiluted sample of ejaculate obtained after twenty-two hours of continence failed to contain any sperm motile or non-motile upon extensive microscopic examination.

One of the advantages of the reinforced polyethylene is that it can be checked visually for tears, excessive holes or loss of the aluminum coating. With pads of porous fabric or paper the loss of the insulating/heat relecting properties of the insulator may not be as apparent. Closed cell foam can be tested by simple pinch test to see if it has continued resistance to compression, thus indicating the continued presence of encapsulated air.

The trapezoid shape was chosen as being most desirable as it is the one flat or sheet form shape that best conforms to the shape of the crotch in use and best accommodates posture changes. The cut-out or "notch" in the trapezoidal insulator is required so that the penis does not press against the top of the insulator pushing it away from the body and reducing its effectiveness. The notch respects the cylindrical shape of the penis by being narrower near the junction of the penis and the scrotum than at the top of the insulator. If the notch were as wide at the bottom as its top, then part of the scrotum would be needlessly exposed.

The trapezoid shape is both easy to manufacture and permits maximum use of the sheet material without needless waste.

It is desirable to size the trapezoid shape to the size of the wearer. The flat insulator must bend to cover the rounded scrotal surface under the molding force given by the undershorts and outer garments. The insulator must be long enough between the base of the notch and the top of the trapezoid to cover the scrotum. It must be more than wide enough to cover the sides of the scrotum completely when molded over the surface of the scrotum but not so wide as to rub against the legs.

The fastener should be placed close to and symmetrically about the center of the area of the insulator. The center of area has the shortest "lever arm" effect for moments about the fastener arising from the surface forces acting on the insulator. The insulator, of course, will wrinkle somewhat in use and in conforming to the scrotum. It is desirable to cut the insulator a little fuller than absolutely necessary. It is inadvisable to trim material at the top and on the sides of the trapezoidal shape in hopes of reducing the wrinkling of it and movement of the insulator. Although at first glance the "wings" of the trapezoid contribute little to scrotal insulation, they in fact provide important coverage when the wearer sits. When triangular sections ranging between 1.3 and 2.4 square inches were cut from either side of the trapezoidal shape both testicles of the wearer were exposed in the ordinary sitting position. Within three weeks of wearing such trimmed inserts, sperm reappeared in the subject who had had zero counts with the full design. Minor trimming (at 15, FIG. 1) to round off sharp edges probably will not impair insulation and may improve comfort slightly.

While the insulator is preferably made with a hook tape fastener so that it may be inserted in regular jockey shorts, it will be appreciated that the insulator could be sold for and used with undershorts that have a special pocket adapted to accommodate the insulator. Instructions can be printed on the face of the insulator to guide the user. Being in flat sheet form, the insulator can be sold conveniently in stacks of a dozen or so as in blister packs.

As has been noted in the literature, oligospermia can be temporarily relieved by heating the scrotum followed by cooling. The present insulator is useful for such a treatment. For example the scrotal insulator can be worn for fourteen days at least fifteen hours each day. Seven weeks after use of the insulator has ceased the scrotum can be cooled for a short period each day for fourteen days. It will be found that sperm concentration will peak approximately two weeks thereafter.

The scrotal insulator of this invention has other attractive features. It interferes neither with the sex act nor preparation for sex. It does not affect general or sexual health. It is simple to use and does not interfere with every day activities.

The present scrotum insulator is, of course, not the total answer. All popular non-surgical methods except abstinence carry some risk of unwanted pregnancy. Even under the best of circumstances the scrotal insulator will not be ideal for all men interested in fertility control. Some men may find close fitting underwear uncomfortable and some may have skin that is too sensitive. The scrotal insulator may be of little value to those who swim or are out in the cold a lot. The long fertility period after use of the insulator begins may make it undesirable for some men.

What is claimed is:

1. As a scrotum insulator, (a) a sheet of flexible insulating material in symmetric trapezoidal form, the base of which is in the range of six to seven inches wide, the top of which is in the range of one and one-half to two and a half inches wide and the height of which is in the range of four and a half to five and a half inches, said base having a centrally located cutout adapted to accomodate the penis, and wherein said sheet is a moisture impervious plastic film having on one side a thin, infra-red-reflective metal layer; (b) fastener means attached to the outer face thereof and adapted to secure said insulator to the undershorts of the user.

2. The insulator of claim 1 wherein said cutout is of trapezoidal shape in the range of one and three-quarters to two and one-quarter inches at the base, three-quarters to one and one-quarter inches at the top and one-half to one inch high.

3. The insulator of claim 1 wherein said flexible insulating material is a reinforced polyethylene sheet vacuum metallized with aluminum over which aluminum is placed a thin protective clear plastic topcoat.

4. The insulator of claim 1 wherein said fastener means covers the geometric center of said outer face.

5. The insulator of claim 1 wherein said fastening means is a flexible hook tape fastener adapted to disengagably secure said insulator to the undershorts of the user.

6. As a scrotum insulator:
(a) a sheet of flexible insulating material in symmetric trapezoidal form, the base of which is in the range of six to seven inches wide, the top of which is in the range of one and one-half to two and a half inches wide and the height of which is in the range of four and a half to five and a half inches, said base having a centrally located cutout adapted to accomodate the penis, and wherein said sheet is a low density, predominantly closed cell plastic foam less than three-eights inch thick;
(b) fastener means attached to the outer face thereof and adapted to secure said insulator to the undershorts of the user.

* * * * *